United States Patent
Boswell et al.

(10) Patent No.: US 7,179,302 B2
(45) Date of Patent: *Feb. 20, 2007

(54) OXIDATIVE TREATMENT OF HAIR WITH REDUCED HAIR DAMAGE

(75) Inventors: Henry Drummond Boswell, Guildford (GB); Jennifer Mary Marsh, Henley-On-Thames (GB); John Scott Park, Aberdeen (GB); Michael Andrew Olshavsky, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/667,878

(22) Filed: Sep. 22, 2003

(65) Prior Publication Data

US 2004/0105830 A1 Jun. 3, 2004

Related U.S. Application Data

(63) Continuation of application No. PCT/US02/08482, filed on Mar. 19, 2002.

(30) Foreign Application Priority Data

Mar. 20, 2001 (GB) .................................. 0106946.7
Nov. 30, 2001 (GB) .................................. 0128749.9

(51) Int. Cl.
*A61K 7/13* (2006.01)

(52) U.S. Cl. ...................... 8/405; 8/406; 8/431; 8/501; 8/542; 424/70.2; 132/202; 132/208

(58) Field of Classification Search ................ 8/405, 8/406, 431, 501, 542; 424/70.2; 132/202, 132/208
See application file for complete search history.

(56) References Cited

U.S. PATENT DOCUMENTS

| 3,542,918 | A | | 11/1970 | Berth ........................... 424/62 |
| 4,138,478 | A | | 2/1979 | Reese ........................... 424/62 |
| 5,009,813 | A | | 4/1991 | Watanabe .................... 252/545 |
| 5,100,436 | A | * | 3/1992 | Wenke ........................... 8/405 |
| 6,004,355 | A | * | 12/1999 | Dias et al. ...................... 8/406 |
| 6,022,381 | A | | 2/2000 | Dias |
| 6,024,891 | A | | 2/2000 | Hughes ................. 252/186.31 |
| 6,177,090 | B1 | | 1/2001 | Dubief |
| 2002/0029429 | A1 | | 3/2002 | Dias |
| 2002/0053110 | A1 | | 5/2002 | Dias |
| 2002/0124329 | A1 | | 9/2002 | Pratt |

FOREIGN PATENT DOCUMENTS

| DE | 4404177 A1 | 8/1995 |
| EP | 1001011 A2 | 5/2000 |
| JP | 11193223 A | 7/1999 |
| WO | WO-94/16672 A1 | 8/1994 |
| WO | WO-97/24106 A1 | 7/1997 |
| WO | WO-98/27944 A1 | 7/1998 |
| WO | WO-02/074273 A1 | 9/2002 |
| WO | WO-02/078661 A2 | 10/2002 |
| WO | WO-02/089754 A1 | 11/2002 |

* cited by examiner

*Primary Examiner*—Eisa Elhilo
(74) *Attorney, Agent, or Firm*—Michael J. Sambrook; Marianne Dressman; Tara M. Rosnell

(57) ABSTRACT

The present invention relates to hair care compositions comprising chelants and methods for reducing oxidative hair damage. The compositions contribute to reducing the oxidative damage sustained by keratinous fibers such as human hair during bleaching, dyeing, perming or other oxidative treatments. The compositions according to the present invention also provide excellent color evenness and color fastness.

15 Claims, No Drawings

OXIDATIVE TREATMENT OF HAIR WITH REDUCED HAIR DAMAGE

CROSS REFERENCE TO RELATED APPLICATION

The application is a continuation of International application PCT/US02/08482 filed on Mar. 19, 2002.

FIELD

The present invention relates to hair care compositions comprising chelants and methods for reducing oxidative hair damage during oxidative treatments of hair such as bleaching, oxidative dyeing or perming.

BACKGROUND

Melanin is a natural pigment found in hair. Melanin and hair-forming cells are naturally produced in the hair bulb at the root of the hair. As new cells are produced, the older ones are pushed upwards out of the skin to form the hair shaft, which is the part of the hair that can be seen above the scalp. Hair can be schematically described as being made of a center part called the cortex, which contains the melanin, and an outer layer called the cuticle. It is the cortex that gives hair its special qualities such as elasticity and curl.

The hair shaft is made of dead cells that have turned into a mixture of different forms of the special hair protein, keratin. Keratin contains high concentrations of a particular amino acid called cystine. Every cystine unit contains two cysteine amino acids in different chains, which have come to lie near each other and are linked together by two sulphur atoms, forming a very strong chemical bond known as a disulphide linkage. This cross-linking by disulphide linkages between the keratin chains accounts for much of the strength of the hair.

Bleaching and dyeing (or coloring) of hair has become increasingly popular over the past years. Younger people may want to change the natural color of their hair to a more fashionable one, while older people may also use dyeing compositions to conceal gray hair. As people grow older, the production of melanin slows, giving more and more gray hair over time. Melanin can be purposely altered by chemical treatments to give lighter shades. The lightening is achieved by oxidizing the melanin pigments, usually with an oxidizing agent in alkaline solution, also called bleaches. Examples of oxidizing agents that can be used are hydrogen peroxide, potassium, sodium or ammonium salts of perborate or percarbonate, persulfate and percarbamide.

Bleaches are also used during oxidative dyeing treatments. Oxidative (or "permanent") dye compositions comprise "precursor dyes" which are small molecules capable of diffusing into the hair. These molecules mainly belong to three classes of aromatic compounds: diamines, aminophenols and phenols. They are sufficiently small to diffuse in the hair shaft where, once activated by an oxidizing agent such as hydrogen peroxide, they further react with other precursors to form larger colored complexes. Oxidative hair dye compositions commonly contain, in addition to the dye precursors and a source of peroxide, a variety of additional cosmetic and peroxide stabilizing agents.

Oxidizing agents can activate oxidative dye precursors across a range of pH. However, it is known that enhanced dye oxidation can be achieved via the use of a hair-swelling agent (HSA) that can adjust the pH of the oxidizing solution. Such HSA's further enhance the oxidizing and dyeing process by swelling the hair fibers to aid both the diffusion of the peroxide and dyeing agents into the hair and enabling faster, more thorough dye oxidization and hair dyeing. Preferred hair-swelling agents for adjusting the pH of peroxide hair oxidizing compositions are aqueous alkaline solutions containing ammonia (ammonium hydroxide) or monoethanolamine(MEA).

Low levels of chelants are routinely used as stabilizers or preservatives in various oxidizing compositions. For example, EDTA (ethylenediaminetetraacetic acid) is commonly used as a stabilizer in hydrogen peroxide solution, which would otherwise decompose too rapidly and could not be stored for a long time. Ethylene diaminedissucinnic acid (EDDS) is also known as a good stabilizing agent component to increase the stability of laundry bleaching products. Amounts as low as 0.1% by weight of the oxidizing composition are usually used to stabilize the oxidizing agent contained in said oxidizing compositions.

Oxidative treatments of hair such as bleaching (decoloration) and oxidative dyeing give good results and are very commonly used. They are however not without drawbacks. The oxidizing agents used for bleaching and oxidative dyeing damage hair to some extent. The mechanism by which damage is caused to the hair fibers is not perfectly understood. However, it is known that some of the disulphide bonds linking the keratin chains break in the presence of oxidizing compositions. Repeated oxidative treatments leave weak, brittle hairs, which have little shine and luster. An enormous effort has been made to address this problem over the past years, and various solutions have been proposed.

Today, most dyeing or bleaching compositions are sold with a conditioner, which is applied on hair after the bleaching or dyeing composition has been rinsed off. Examples of conditioning agents are silicones, cationic surfactants and cationic polymers. However efficient, conditioners cannot prevent successive chemical treatments causing premature hair breakage. In fact, conditioners do not bring the hair back to its initial condition but merely conceal the damage under a protective layer of the conditioning agent, which only results in an improved feel of the hair.

Attempts have been made to protect the hair from damage instead of merely concealing it. U.S. Pat. No. 5,100,436 discloses hair dyeing compositions comprising metal-chelant complexes. The use of catalytic amounts of dipyridyl or o-phenanthroline complexes (0.001 to 0.1% by weight of the solution) allows a reduction in the time of exposure, thus reducing the damage caused by the oxidizing agent.

U.S. Pat. No. 6,013,250 discloses composition for treating hair against chemical and photo damage by the use of hydrolyzed proteins having an abundance of anionic amino acids and in particular, sulphur-containing amino acids. These proteins serve as "decoys", in order to minimize the damage caused to the natural disulphide bonds.

U.S. Pat. No. 4,138,478 discloses agents for reducing the damage to hair during bleaching and dyeing by the use of a water-soluble 3-amino-1-hydroxypropane-1,1-diphosphonic compound for protecting hair from damage by "nascent oxygen". According to this patent, "the diphosphonic compound is substantively adsorbed by the hair and acts to hinder degradation of the hair by nascent oxygen which is either present therewith or which is substantially added". Other protective compounds such as hydroxyethane-1,1 diphosphonic acid (HEDP) and ethylenediaminetetramethylene phosphonic acid (EDTMP) are disclosed at low levels in U.S. Pat. No. 3,202,579 and U.S. Pat. No. 3,542,918.

"Properties of peroxide-bleached hair" (W. Edman & E. Marti, J. Soc. Cosmet. Chem., 1960, p.133), discloses that an aqueous solution of hydrogen peroxide is stabilized by adding 0.1% by weight of the bleaching composition of tetrasodium salt of EDTA (ethylenediamine tetraacetic acid) and that damage to hair can be prevented by adding 0.1% of the tetrasodium salt of EDTA to the aqueous bleaching compositions. However, is has now been surprisingly found that EDTA, although widely used in bleaching and dyeing compositions, displays very little benefits, unless utilized at levels much higher than 0.1%.

Chelants in hair care compositions have been used to remove minerals bound to hair. For example, U.S. Pat. No. 5,635,167 discloses a process for the removal of exogenous metal ions that have become attached to hair. The treatment comprises a step wherein hair is contacted with a blend of chelating agents (selected from the group consisting of amino acid chelating agents, polyphosphate chelating agents and phosphonate chelating agents) at a pH of between 4 and 9 and at a concentration of between 4% to 25% by weight.

WO97/24106, Dias et al. discloses hair coloring compositions comprising a water soluble peroxygen-bleach, a bleaching aid selected from organic peroxyacid bleach precursors and preformed organic peroxyacids and one or more hair coloring agents. Various chelants are disclosed as optional ingredients and exemplified in hair care compositions at 0.1% by weight of the composition. The organic peroxy acid bleach precursors are defined as organic compounds that react with hydrogen peroxide in a perhydrolysis reaction to produce a peroxyacid. These bleaching aids are claimed to provide benefits including reduced hair damage at lower pH. However, the Applicant has found that at a pH higher than 8, these bleaching aids are much more damaging to hair than usual water-soluble oxidizing agents such as hydrogen peroxide. Without being bound by theory, the Applicant believes that the conjugate base of the organic peroxyacid formed at a pH above 8 is more likely to oxidize the disulphur bonds of the keratin than other oxidizing agents such as hydrogen peroxide. Additionally, hair coloration, especially with oxidative dyes is much poorer at pH 8 than pH 10, which is another advantage of this invention over WO9724106. Finally peroxyacid precursors are difficult to solubilize, especially in oil-in-water emulsion.

Despite these developments, damage to hair caused by the strongly aggressive chemicals contained in most bleaching, dyeing or perming compositions particularly with repeated usage is still a problem, particularly at high pH.

It is hence an object of the present invention to provide new compositions capable of improved protection of keratinous fibers such as human hair from oxidative damage, in particular the structurally important keratin bonds such as the disulphide bonds from oxidative breakage.

It is another object of this invention to provide bleaching, dyeing or perming compositions with a better efficiency in terms of light shade, color evenness, color fading and hair feel.

It is another object of this invention to provide bleaching or dyeing compositions capable of protecting keratinous fibers such as hair while at the same time delivering a good lightening effect.

It is another object of the present invention to provide methods of treating hair with chelants for reducing oxidative hair damage.

It has now been surprisingly found that chelants have excellent damage inhibiting properties. None of the above-mentioned references disclose the compositions of the present invention.

SUMMARY

The subject of the present invention is a composition suitable for use during a hair treatment comprising:

a) an oxidizing agent;

b) a chelant;

wherein said chelant is in an amount sufficient to provide a damage benefit equivalent to less than 160, preferably less than 140, more preferably less than 120, even more preferably less than 110 cysteic acid units as measured by the FT-IR Damage Assessing Protocol after a 5-Cycle Oxidative Hair Treatment Protocol With 2 Intermediate Washes as defined herein and/or to provide a damage benefit equivalent to a Normalized Shine Ratio of at least 0.80, preferably at least 0.85, more preferably at least 0.95, even more preferably at least 0.99 as measured by the Goniophotometer Damage Assessing Protocol after a 5-Cycle Hair Oxidative Treatment Protocol With 10 Intermediate Washes as described herein.

DETAILED DESCRIPTION

While the specification concludes with claims which particularly point out and distinctly claim the invention, it is believed the present invention will be better understood from the following description.

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

As used herein, the term "oxidizing composition" means a composition comprising at least one oxidizing agent suitable for use on hair, such as hydrogen peroxide, sodium, potassium, ammonium or other salts of perborate, percarbonate, persulfate and percarbamide. Examples of such compositions are oxidative dye compositions and bleaching compositions.

As used herein the term "oxidative treatment of hair" or a "hair treatment comprising at least one oxidative step" is used in the broad sense in that it is intended to encompass all treatments of hair comprising at least one step of contacting hair with at least one oxidizing composition. Examples of oxidative treatment for human hair are bleaching, dyeing or perming.

As used herein the term "immediately" means within about 1 hour, preferably within about 30 nm, more preferably within about 15 nm.

As used herein the term "log x" refers to the common (or decimal) logarithm of x.

All percentages are by weight of the total composition unless specifically stated otherwise. When more than one composition are used during a treatment, the total weight to be considered is the total weight of all the compositions applied on hair simultaneously (i.e. the weight found "on head") unless otherwise specified. All ratios are weight ratios unless specifically stated otherwise.

All cited references are incorporated herein by reference in their entireties. Citation of any reference is not an admission regarding any determination as to its availability as prior art to the claimed invention.

Chelants

Definition

The term "chelant" (or "chelating agent" or "sequestering agent") is well known in the art and refers to a molecule or a mixture of different molecules each capable of forming a chelate with a metal ion. A chelate is an inorganic complex in which a compound (chelant) is coordinated to a metal ion at two or more points so that there is a ring of atoms including the metals. Chelants contain two or more electron donor atoms that form the coordination bonds with the metal ion.

Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference.

When related to chelants, the terms "salts and derivatives thereof" mean all salts and derivatives comprising the same functional structure as the chelant they are referring to and that have similar or better chelating properties. These terms include alkali metal, alkaline earth, ammonium, substituted ammonium salts (e.g monoethanolammonium, diethanolammonium, triethanolammonium), esters of chelants having an acidic moiety and mixtures thereof, in particular all sodium, potassium or ammonium salts. The term "Derivatives" also includes "chelating surfactant" compounds (these are chelants modified to bear a surfactant moiety while keeping the same chelating functionality, see U.S. Pat. No. 5,284,972, "N-acyl-N,N',N'-ethylenediaminetriacetic acid" for an example of modified ethylenediaminetriacetic acid). The term "Derivatives" also includes large molecules comprising one or more chelating groups having the same functional structure as the parent chelants. Examples of these large molecules is polymeric EDDS (ethylenediaminedisuccinic acid) made of unit block according to the following structure:

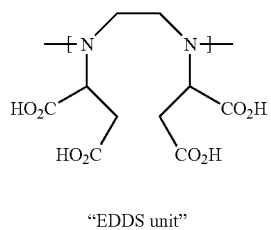

"EDDS unit"

and disclosed in U.S. Pat. No. 5,747,440 Kellett et al.

Preferred chelants for use herein are carboxylic acids (in particular aminocarboxylic acids), phosphonic acids (in particular aminophosphonic acids) and polyphosphoric acids (in particular linear polyphosphoric acids), their salts and derivatives.

Aminocarboxylic Acid Chelants

Carboxylic acid chelants as defined herein are chelants having at least one carboxylic acid moiety (—COOH).

Examples of aminocarboxylic acid chelants suitable for use herein include nitrilotriacetic acid and polyaminocarboxylic acids such as diethylenetriamine pentaacetic acid (DTPA), ethylenediamine disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N-N'-diglutaric acid (EDDG), 2-hydroxypropylenediamine-N-N'-disuccinic acid (HPDDS), ethylenediaminetetraacetic acid (EDTA), salts thereof and derivatives thereof.

Other suitable aminocarboxylic chelants for use herein are iminodiacetic acid derivatives such as N-2-hydroxyethyl N,N diacetic acid or glyceryl imino diacetic acid (described in EP-A-317,542 and EP-A-399,133), iminodiacetic acid-N-2-hydroxypropyl sulfonic acid and aspartic acid N-carboxymethyl N-2-hydroxypropyl-3-sulfonic acid (described in EP-A-516,102), β-alanine-N,N'-diacetic acid, aspartic acid-N,N'-diacetic acid, aspartic acid-N-monoacetic acid and iminodisuccinic acid chelants (described in EP-A-509,382), ethanoldiglycine acid, salts thereof and derivatives thereof.

EP-A-476,257 describes suitable amino based chelants. EP-A-510,331 describes suitable chelants derived from collagen, keratin or casein. EP-A-528,859 describes a suitable alkyl iminodiacetic acid chelants. Dipicolinic acid and 2-phosphonobutane-1,2,4-tricarboxylic acid are also suitable.

Preferred aminocarboxylic chelants are diamine-N,N'-dipolyacid and monoamine monoamide-N,N'-dipolyacid chelants, salts thereof and derivatives thereof. Preferred polyacids contain at least two acid groups independently selected from the carboxylic acid group (—COOH), sulphonic group (—SO$_3$H), the o-hydroxyphenyl group, the m-hydroxyphenyl group and the p-hydroxyphenyl group. Suitable polyacids include diacids, triacids and tetraacids, preferably diacids. Preferred salts include alkali metal, alkaline earth, ammonium or substituted ammonium salts. EDTA is a tetramonoacid and does not belong to this class of preferred chelants.

Preferably, the polyacids are di-carboxylic acids, preferably di-carboxylic acids having a carbon chain length of from about 3 to about 10 carbon atoms, more preferably from about 4 to about 6 carbon atoms, even more preferably about 4 carbon atoms.

Exemplary diamine dipolyacids suitable for use herein include ethylenediamine-N,N'-disuccinic acid (EDDS), ethylenediamine-N,N'-diglutaric acid (EDDG), 2-hydroxypropylenediamine-N,N'-disuccinic acid (HPDDS), all disclosed in European Patent EP0687292, ethylenedicysteic acid (EDC) disclosed in U.S. Pat. No. 5,693,854, diaminoalkyldi (sulfosuccinic acids) (DDS) disclosed in U.S. Pat. No. 5,472,642 and EDDHA (ethylenediamine-N-N'-bis(ortho-hydroxyphenyl acetic acid)), a method of preparation of which is disclosed in EP331556. A preferred monoamine monoamide-N,N'-dipolyacid is glycinamide-N,N'-disuccinic acid (GADS), described in U.S. Pat. No. 4,983,315.

Highly preferred for use herein is ethylenediamine-N,N'-disuccinic acid (EDDS), derivatives and salts thereof. Preferred EDDS compounds for use herein are the free acid form, and salts thereof. Preferred salts include alkali metal, alkaline earth metals, ammonium and substituted ammonium salts (e.g. monoethanolammonium, diethanolammonium, triethanolammonium). Highly preferred salts are sodium, potassium, magnesium and calcium salts. Examples of such preferred sodium salts of EDDS include Na$_2$EDDS and Na$_3$EDDS.

The structure of the acid form of EDDS is as follows:

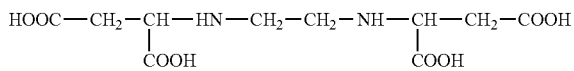

EDDS can be synthesised, for example, from readily available, inexpensive starting materials such as maleic anhydride and ethylenediamine. The synthesis of EDDS from maleic anhydride and ethylene diamine yields a mixture of three optical isomers, [R,R], [S,S], and [S,R] (25% S,S, 50% R,S and 25% R,R), due to the two asymmetric carbon atoms. The biodegradation of EDDS is optical isomer-specific, with the [S,S] isomer degrading most rapidly and extensively.

U.S. Pat. No. 5,747,440, Kellett et al., discloses EDDS derivatives comprising an modified polyamine having units of the formula:

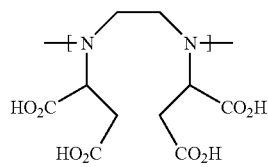

"EDDS unit"

Preferred aminocarboxylic acid chelants that are not diamine-N,N'-dipolyacid and monoamine monoamide-N,N'-dipolyacid chelants include N,N'-bis(2-hydroxybenzyl) ethylenediamine-N,N'-diacetic acid (HBED) salts thereof and derivatives thereof:

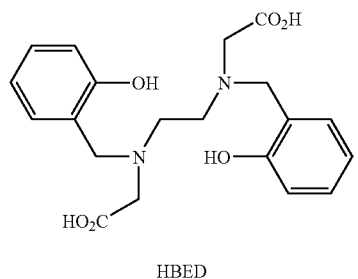

HBED

Examples of suitable HBED derivatives can be found in WO9744313.

Polyphosphoric Acid Chelants

Suitable polyphosphoric acid type chelants include molecules that contain more than one P atom and have P—O—P bonds. Polyphosphoric acid chelants and salts (polyphosphates) can be linear and are generally represented by the formula $[P_nO_{3n+1}]^{(n+2)-}M_{(n+2)}^+$ wherein M is a suitable counter-ion such as $H^+$, $Na^+$ or $K^+$ and n an integer. Polyphosphoric acid type chelants and their polyphosphate salts can also be cyclic and have the formula $[P_nO_{3n}]^{n-}M_n^+$. Representative examples include, among other, sodium tripolyphosphate, tetrasodium diphosphates, hexametaphosphoric acid and sodium metaphosphate.

Phosphonic Acid Chelants

Suitable phosphonic acid type chelants include amino alkylene poly (alkylene phosphonic acid), ethane 1-hydroxy diphosphonic acids and nitrilo trimethylene phosphonic acids, salts thereof and derivatives thereof. Suitable chelants of this type are disclosed in U.S. Pat. No. 4,138,478, Reese et al., U.S. Pat. No. 3,202,579 and U.S. Pat. No. 3,542,918, Berth et al, all incorporated herein by reference.

Preferred phosphonic acid type chelants for use herein have the formula (I) below:

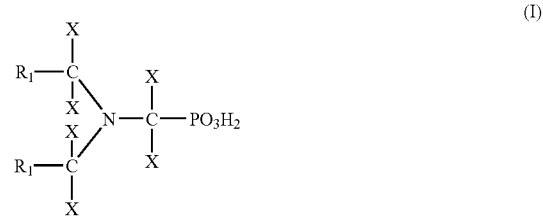

wherein each X are independently selected from hydrogen or alkyl radicals, preferably hydrogen or alkyl radicals having from 1 to 4 carbon atoms, preferably hydrogen; and each $R_1$ are independently selected from —$PO_3H_2$ or a group having the formula (II) below:

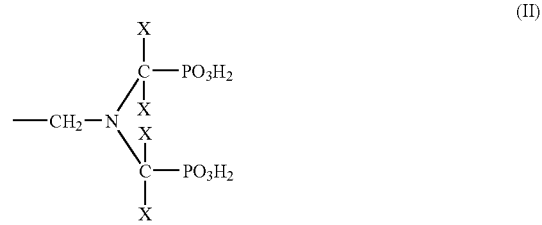

Preferred chelants according to Formula (I) for use herein are aminotri-(1-ethylphosphonic acid), ethylenediamine-tetra-(1-ethylphosphonic acid), aminotri-(1-propylphosphonic acid), aminotri-(isopropylphosphonic acid) and chelants having the formula (III) below:

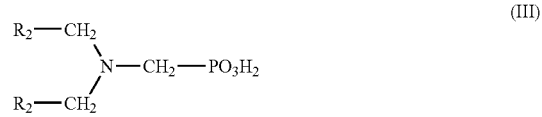

wherein each $R_2$ are independently selected from —$PO_3H_2$ or a group having the formula (IV) below:

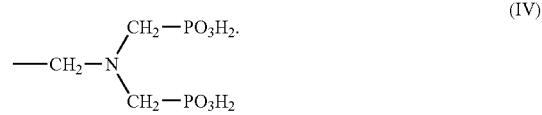

Especially preferred chelants according to formula (III) for use herein are aminotri-(methylenephosphonic acid), ethylene-diamine-tetra-(methylenephosphonic acid) (EDTMP) and diethylene-triamine-penta-(methylenephosphonic acid) (DTPMP).

Examples of Other Chelants:

Examples of other chelants suitable for use herein include but are not limited to polyethyleneimines as disclosed in U.S. Pat. No. 5,955,415.

Levels

Chelants must be present in the composition at a level sufficient to provide a benefit measurable by the FT-IR Damage Assessing Protocol after a 5-Cycle Oxidative Hair Treatment Protocol With 2 Intermediate Washes and/or by the Goniophotometer Damage Assessing Protocol after a 5-Cycle Hair Oxidative Treatment Protocol With 10 Intermediate Washes, both of which are defined herein.

Levels of chelants in the oxidizing compositions or in pre-treat compositions can be as low as about 0.25%, preferably at least about 0.5% for the most effective chelants such as diamine-N,N'-dipolyacid and monoamine monoamide-N,N'-dipolyacid chelants (for example EDDS). Less effective chelants will be more preferably used at levels of at least about 1%, even more preferably above about 2% by weight of the composition, depending of the efficiency of the chelant. Levels as high as about 10% can be used, but above this level significant formulation and/or human safety issues arise. Levels above about 4% can be used but will usually not result in additional damage benefit.

Damage Prevention

The Applicant has surprisingly found that chelants could efficiently prevent oxidative hair damage when formulated in level higher than previously mentioned in the literature or formulated in commercial compositions. Levels of chelants used in the prior art are, at best, too low to be really useful and sometimes totally inefficient (See Experimentals). This is particularly true for formulations with rheologies greater than water such as oil-in-water emulsions or thickened aqueous solutions.

Oxidative hair damage can be measured by the FT-IR Damage Assessing Protocol and/or by the Goniophotometer Damage Assessing Protocol, both described below.

It is was found that it is highly relevant for the consumer that oxidizing compositions comprise a chelant or a mixture of chelants in an amount sufficient to provide a damage benefit equivalent to:

a) less than 160, preferably less than 140, more preferably less than 120, even more preferably less than 110 cysteic acid units as measured by the FT-IR Damage Assessing Protocol after a 5-Cycle Oxidative Hair Treatment Protocol as defined below; and/or b) a Normalized Shine Ratio of at least 0.80, preferably at least 0.85, more preferably at least 0.95, even more preferably at least 0.99 as measured by the Goniophotometer Damage Assessing Protocol after a 9-Cycle Hair Oxidative Treatment Protocol as described herein.

Conditional Stability Constants of Preferred Chelants

Good results such as those described above can be achieved by increasing the levels of previously used chelants or by using level of select chelants that were found to be particularly efficient even at low levels. These particularly efficient chelants have a much stronger affinity for transition metal ions such as $Cu^{2+}$ than for alkaline-earth metal ions such as $Ca^{2+}$ at pH 10. One relatively easy way of predicting how well a chelant will perform is calculating the ratio of the log of the Conditional Stability Constant of the chelant for $Cu^{2+}$ to the log of the Conditional Stability Constant of the chelant for $Ca^{2+}$ at pH 10 as described below.

The Conditional Stability Constant is a parameter commonly used in the art to practically assess the stability of metal-chelant complex at a given pH. A detailed discussion on Conditional Stability Constant can be found for example in "Dow chelating agents" published by the Dow Chemical Company Limited, incorporated herein by reference.

The Stability constant of a metal chelant interaction can be defined as:

$$K_{ML} = \frac{[ML]}{[M][L]}$$

Where:

[ML]=Concentration of metal chelant complex at equilibrium

[M]=Concentration of free metal ion

[L]=Concentration of free chelant $K_{ML}$=Stability constant for the metal chelant complex Wherein all concentrations are expressed in $mol/dm^3$. Stability constants are conveniently expressed as logarithms. The values of the logarithms of the Stability constant values for some exemplary metal ion-chelant complexes are given in the following table:

TABLE 1

Log Stability constants for 1:1 complexes of various chelants with Cu and Ca [1] (fully deprotonated chelants)

| | log K* | |
|---|---|---|
| Agent | Cu | Ca |
| EDDS | 18.35 | 4.58 |
| DTPMP | 19.5 | 7.1 |
| EDTMP | 23.2 | 9.36 |
| DTPA | 21.4 | 10.75 |
| HEDP | 11.84 | 6.0 |
| EDTA | 18.78 | 10.65 |
| EDDHA | 25.3 | 7.2 |

*All measured at 25 deg and 0.1 M ionic strength
Most chelants have a degree of protonation that is dependent on pH. This can be expressed using chelant proton Stability constants (stepwise K).

These Stability constants are obtained from the equation below:

$$H + LHn \rightleftharpoons LH_{n+1}$$

$$K_{Hn+1} = \frac{[LH_{n+1}]}{[H][LH_n]}$$

The values of the proton chelant Stability constant for some usual chelants are given in the tables below:

TABLE 2a

| log protonation constants for tetra-protonated chelants [1] | | | | |
|---|---|---|---|---|
| | $HL^{3-}$ | $H_2L^{2-}$ | $H_3L^-$ | $H_4L$ |
| $EDDS^{4-}$ | 10.01 | 6.84 | 3.86 | 2.95 |
| $HEDP^{4-}$ | 10.8 | 6.88 | 2.53 | 1.8 |

TABLE 2a-continued log protonation constants for tetra-protonated chelants [1]

|  | $HL^{3-}$ | $H_2L^{2-}$ | $H_3L^-$ | $H_4L$ |
|---|---|---|---|---|
| EDTA $^{4-}$ | 10.19 | 6.13 | 2.69 | 2.00 |
| EDDHA $^{4-}$ | 12.1 | 9.5 | 8.5 | 6.3 |

TABLE 2b log protonation constants for penta-protonated chelants [1]

|  | $HL^{4-}$ | $H_2L^{3-}$ | $H_3L^{2-}$ | $H_4L^-$ | $H_5L$ |
|---|---|---|---|---|---|
| DTPA $^{5-}$ | 10.48 | 8.60 | 4.28 | 2.6 | 2.0 |

TABLE 2c log protonation constants for hepta-protonated chelants [1]

|  | $HL^{6-}$ | $H_2L^{5-}$ | $H_3L^{4-}$ | $H_4L^{3-}$ | $H_5L^{2-}$ | $H_6L^-$ | $H_7L$ |
|---|---|---|---|---|---|---|---|
| EDTMP $^{7-}$ | 13.0 | 9.78 | 7.94 | 6.42 | 5.17 | 3.02 | 1.30 |

TABLE 2d log protonation constants for octa-protonated chelants [1]

|  | $HL^{7-}$ | $H_2L^{6-}$ | $H_3L^{5-}$ | $H_4L^{4-}$ | $H_5L^{3-}$ | $H_6L^{2-}$ | $H_7L^-$ | $H_8L$ |
|---|---|---|---|---|---|---|---|---|
| DTPMP $^{8-}$ | 12.0 | 10.10 | 8.15 | 7.17 | 6.38 | 5.50 | 4.45 | 2.8 |

[1] = Arthur Martell & Robert M Smith, Critically Selected Stability Constants of Metal Complexes Database, Version 3.0

The stability constants of chelant-metal ion complexes are well documented in the literature for commonly used chelants (see for example=Arthur Martell & Robert M Smith, Critically Selected Stability Constants of Metal Complexes Database, Version 3.0 and above, incorporated herein by reference). When not documented the constants can still be measured using various analytical methods (see "Metal Complexes in Aqueous Solutions", Martel and Hancock, edition Modem Inorganic Chemistry, p.226–228, incorporated herein by reference).

The gradual change in chelant species as pH changes can be represented using alpha coefficients ($\alpha_{HL}$), defined as $$\text{Alpha coefficient (at a given pH)} = \frac{\text{Total concentration of ligand}}{\text{Free ligand concentration}}$$

In the case of tetra-acid chelants the values can be calculated from $$\alpha_{HL} = 1 + K_1[H] + K_1K_2[H]^2 + K_1K_2K_3[H]^3 + K_1K_2K_3K_4[H]^4$$

A further factor affecting metal chelant interactions is the tendency of metals to form hydroxide species as the pH increases. This effect can be represented using metal alpha values [2] as summarised in the table below at pH 10:

TABLE 3 log alpha values for metal ions [2]

| pH | $Ca^{2+}$ | $Cu^{2+}$ |
|---|---|---|
| 10 | 0.0 | 2.00 |

[2] = A Ringbom & E Wanninen, Treatise on Analytical Chemistry, 2nd Ed, 1979, Part 1, Vol 2

By combining Stability constants and alpha constants at pH 10 we can use the formula below to give the effective chelating power of a chelant. This is the Conditional Stability Constant referred to in this Patent Application.

$$K_{ML}(cond) = \frac{K_{ML}}{\alpha_M \cdot \alpha_{HL}}$$

log $K_{ML}$(cond) = log $K_{ML}$ − log $\alpha_{HL}$ − log $\alpha_M$

The data for a range of chelants with Cu and Ca is given below:

| | log Conditional Stability Constant (pH 10) | | |
|---|---|---|---|
| Chelant | Cu | Ca | Ratio Cu/Ca |
| EDDHA | 21.04 | 4.97 | 4.23 |
| EDDS | 16.04 | 4.27 | 3.76 |
| DTPMP | 15.14 | 4.74 | 3.19 |
| EDTMP | 17.99 | 6.15 | 2.92 |
| DTPA | 18.78 | 10.13 | 1.85 |
| HEDP | 8.98 | 5.13 | 1.75 |
| EDTA | 16.37 | 10.24 | 1.60 |

The applicant has surprisingly found that levels as low as 0.25% by weight of chelants having a ratio $$\frac{\log K_{CuL}}{\log K_{CaL}}$$

(wherein log $K_{CuL}$ is the common logarithm of the Conditional Stability Constant between this chelant and $Cu^{2+}$ and wherein log $K_{CaL}$ is the common logarithm of the Conditional Stability Constant between this chelant and $Ca^{2+}$, both at pH 10) of at least 3.20 give good oxidative damage protection. This $$\frac{\log K_{CuL}}{\log K_{CaL}}$$

ratio should preferably be at least 3.30, more preferably at least 3.40, even more preferably at least 3.50 at pH 10. It is important to calculate this ratio at pH 10 because oxidizing compositions for treating hair usually have a pH of from 8 to 12. Using stability constants without taking into account the influence of the pH is a common mistake and will give misleading results for the purpose of identifying chelants that will prevent oxidative damage at low levels.

Hydrogen Peroxide Decomposition Ratio (% Loss)

It is preferred that the complexes formed by these preferred chelants efficiently inhibit the red-ox chemistry of $Cu^{2+}$. The ability of chelants to inhibit the red-ox chemistry of the chelated copper metal ion can be effectively compared using their Hydrogen Peroxide Decomposition Ratio (% Loss) as measured by the Hydrogen Peroxide Decomposition Ratio Measurement Protocol described hereafter in the "EXPERIMENTALS" section.

The table below shows the Hydrogen Peroxide Decomposition Ratio (% Loss) for different chelants:

| Chelant | Peroxide % at t = 0 | Peroxide % at t = 30 mn | % Loss |
|---|---|---|---|
| EDTA | 3.576 | 3.573 | 0.1% |
| EDDS | 3.150 | 3.104 | 1.5% |
| DTPMP | 3.078 | 2.964 | 3.7% |
| MGDA | 3.498 | 3.104 | 11.3% |
| HEDP | 4.126 | 2.792 | 32.3% |
| No chelant | 0.563 | — | 100% |

MGDA is methylglycinediacetic acid and forms a pentadentate complex with $Cu^{2+}$.

Chelants forming hexadentate type complexes with $Cu^{2+}$ were found to adequately inhibit the red-ox chemistry of the metal ion ("hexadendate complex" means that the chelant forms six bonds with the chelated metal ion). Examples of chelants that form such complexes with $Cu^{2+}$ are EDDS, HBED, EDTA and EDDHA. Forming such complexes efficiently prevents the chelated heavy metal ion from reacting with the molecule of the oxidizing agent, for example hydrogen peroxide.

As the table above shows, EDTA has a very good capacity at inhibiting the red-ox chemistry of copper. This was a very surprising finding for the inventors because experiments had shown that EDTA had very poor damage prevention properties in "real" conditions of use wherein the concentration of transition metal ion such as copper and alkaline-earth metal ion such as $Ca^{2+}$ are high compared to lab-condition wherein the water is de-ionized for experiments. (see EXPERIMENTALS hereinbelow). The Applicant believes that this clearly shows that the ratio $$\frac{\log K_{CuL}}{\log K_{CaL}}$$

at pH 10 is an essential parameter to use in order to determine the oxidative damage prevention efficiency of chelants in real conditions of use.

Without being bound by theory, it is believed that chelants act to chelate environmental and intrinsic heavy metal ions such as iron, manganese and copper. In the absence of chelants, these heavy metal ions react with hydrogen peroxide to give highly damaging species such as free radicals, which are believed to be very harmful to the disulphide bonds of hair. It is believed that alkaline-earth metal ions such as $Ca^{2+}$ compete with heavy metal ions to form complexes with the chelants, therefore chelants with a much higher affinity for $Cu^{2+}$ than for $Ca^{2+}$ will much more efficiently prevent oxidative damage than chelants with a lower relative affinity for $Cu^{2+}$. The Applicant believes that the importance of measuring damage under real life conditions (i.e. at pH 10 and with non-deionized water) was never recognized or foreseen until now.

Oxidizing Agent

The compositions according to the present invention comprise or are used in combination with a composition that comprises at least one oxidizing agent. Preferred oxidizing agents for use herein are water-soluble peroxygen oxidizing agents. "Water-soluble" as defined herein means that in standard condition at least 0.1 g, preferably 1 g, more preferably log of said oxidizing agent can be dissolved in 1 liter of deionized water. The oxidizing agents are valuable for the initial solubilisation and decolorisation of the melanin (bleaching) and accelerate the polymerization of the oxidative dye precursors (oxidative dyeing) in the hair shaft.

Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Mixtures of two or more such oxidizing agents can be used if desired. Preferred for use in the compositions according to the present invention is hydrogen peroxide.

In conventional dyeing and bleaching compositions, levels of peroxygen oxidizing agent are usually of from about 0.1% to about 7% by weight. Higher levels, whilst giving good results in term of efficacy were until now not practical because of increased hair damage. The oxidative damage protection provided by the present invention makes it now possible to use oxidizing agent such as hydrogen peroxide in level up to 40% in the oxidizing composition. However, for safety reasons, level above 12% should be carefully investigated before being used on human. Preferably, the level of the oxidizing agent in the oxidizing composition is of from about 0.5% to about 20% by weight, more preferably of from about 1% to about 15%. The compositions according to the present invention provide excellent gray coverage, vibrant colors and acceptable damage at level above about 7% (typically about 12%).

The weight ratio of oxidizing agent to oxidative damage inhibiting chelant (e.g. EDDS) is preferably in the range of from 50:1 to 1:50, preferably from 25:1 to 1:25, more preferably from 15:1 to 1:15, even more preferably of from 9:1 to 1:10.

Additional Components

Moreover, it is also intended that the compositions of the present invention may be complex compositions, which in addition to the chelant and oxidizing agent comprise other components that may or may not be active ingredients. This includes, but is not limited to, buffering agents, hair dyeing agents such as oxidative dye precursors, non-oxidative dyes, thickeners, solvents, enzymes, anionic, non ionic, amphoteric and cationic surfactants, conditioning agents, carriers, antioxidants, stabilizers, perming actives, perfume, hair swelling agents and/or polymers. Some of these additional components are detailed hereafter.

It is preferred, however, that the composition according to the present invention should preferably be substantially free from sodium nonanoylbenzenesulfonate (NOBS), acetyltriethylcitrate (ATC), sodium (6-nonaamidocaproyl)oxybenzenesulfonate, peracetic and pemanoic acid since they have a negative effect on the efficiency of bleaching and coloring and increase damage at a pH above 8. The composition should be substantially free from organic peroxyacid precursors and preformed organic peroxyacid, such as those defined in WO97/24106. The term substantially free as used herein means that the compositions according to the present invention should comprise less than 1.5%, preferably less than 1%, more preferably less than 0.5%, even more preferably less than 0.1%, still more preferably 0% by weight of the composition of such compounds.

It is might be also preferred that the compositions of the present invention are substantially free of inorganic phosphate or phosphonate compounds since they are usually non- or poorly biodegradable.

Finally, the compositions according to the present invention can be provided in any usual form, such as for example an aqueous composition, a powder, a gel or an oil-in-water emulsion. Preferred media for the compositions according to the present invention are thickened solutions comprising a salt-tolerant thickener or oil-in-water emulsions.

pH Buffering Agents

The compositions according to the present invention preferably further comprise a pH buffering agent. The pH of the composition is preferably of from about 8 to about 12, more preferably of from about 9 to about 11, even more preferably of from about 9.5 to about 10.5. Suitable buffering agents are well known in the art and include for example ammonia/ammonium acetate mixture and monoethanolamine (MEA).

Oxidative Hair Dye Precursors

These compounds are well known in the art, and include aromatic diamines, aminophenols and their derivatives (a representative but not exhaustive list of oxidation dye precursor can be found in Sagarin, "Cosmetic Science and Technology", Interscience, Special Edn. Vol. 2 pages 308 to 310). Precursors can be used with couplers. Couplers are generally colorless molecules that can form colors in the presence of activated precursors.

The choice of precursors and couplers will be determined by the color, shade and intensity of coloration that is desired. The precursors and couplers can be used herein, singly or in combination, to provide dyes having a variety of shades ranging from ash blonde to black.

Hair dye compositions will generally comprise from about 0.001% to about 10%, preferably from about 0.1% to about 2%, of oxidative dye precursors and couplers.

Thickeners

The composition of the present invention may optionally further comprise at least about 0.1% of thickeners. Thickeners are preferably comprised in amount sufficient to provide the composition with a viscosity of from about 1 Pa.s to 10 Pa.s (1,000 to 10,000 cP) at 26° C. in order to provide a composition that can be readily applied to the hair without dripping.

Preferred for use herein are salt tolerant thickeners. Salt-tolerant thickeners are functionally defined herein as compounds that increases the viscosity of an aqueous composition consisting of 3.8% DTPMP (tetrasodium salt) and 1.95% NH3 to at least 1 Pa.s (1,000 cP) when incorporated at levels of 2% by weight as measured at 26.7° C. The viscosity can be measured with a Brookfield viscometer DVII, using S41 spindles for samples under 10 Pa.s (10,000 cP) and spindle S52 for samples over 10 Pa.s (10,000 cP) (available from Brookfield), with a speed rating of 1 revolution per minute and samples sizes of 2 ml (for S41 spindle) or 0.5 ml (for S52 spindle).

A non exclusive list of suitable salt tolerant thickeners for use herein include xanthan, guar, hydroxypropyl guar, scleroglucan, methyl cellulose, ethyl cellulose (commercially available as Aquacote®), hydroxyethyl cellulose (Natrosol®), carboxymethyl cellulose, hydroxypropylmethyl cellulose, microcrystalline cellulose, hydroxybutylmethyl cellulose, hydroxypropyl cellulose (Klucel®), hydroxyethyl ethyl cellulose, cetyl hydroxyethyl cellulose (Natrosol® Plus 330), N-vinylpyrollidone (Povidone®), Acrylates/Ceteth-20 Itaconate Copolymer (Structure® 3001), hydroxypropyl starch phosphate (Structure® ZEA), polyethoxylated urethanes or polycarbamyl polyglycol ester (e.g. PEG-150/Decyl/SMDI copolymer=Aculyn® 44, PEG-150/Stearyl/SMDI copolymer=Aculyn 46®), trihydroxystearin (Thixcin®) acrylates copolymer (e.g. Aculyn® 33) or hydrophobically modified acrylate copolymers (e.g. Acrylates/Steareth-20 Methacrylate Copolymer=Aculyn® 22).

Fatty alcohols have thickening properties and can be used in the compositions of the present invention. Fatty alcohols are however not salt-tolerant thickeners according to the above definition. A mixture of 2% cetyl and stearyl alcohol has for example a viscosity of less than about 0.7 Pa.s (700 cP) as measured at 26° C. with a Brookfield viscometer in the conditions disclosed hereabove.

Conditioning Agent

The compositions of the present invention preferably, but not necessarily, further comprises at least one conditioning agent. Preferred conditioning agents are selected from silicone materials, especially nonvolatile silicone and amino functionalised silicones, cationic surfactants, cationic polymers and mixtures thereof.

The conditioning agent will generally be used at levels of from about 0.05% to about 20% by weight of the composition, preferably of from about 0.1% to about 15%, more preferably of from about 0.2% to about 10%, even more preferably of from about 0.2% to about 2%. The minimum level that is used in a particular composition should be effective to provide a conditioning benefit. The maximum level that can be used is not limited by theory, but rather by practicality. It is generally unnecessary and expensive to use levels in excess of about 10% and, depending on the type of agent (polymeric conditioners being most prone), such high levels can cause an undesirable weighting down of the hair.

Suitable conditioning agents are disclosed in WO9804237 p.22–p.29, and in WO9632919 p.17–22 both incorporated herein by reference.

EXPERIMENTALS

All results discussed herein were obtained by testing chelants according to the following protocols. The chelants tested can be obtained from any usual supplier.

Hydrogen Peroxide Decomposition Ratio Measurement Protocol

The Hydrogen Peroxide Decomposition Ratio Measurement Protocol is defined as follows: 6.0% by weight of concentrated ammonium hydroxide (30% active ammonia) is added to deionised water and the pH of the solution is adjusted to 10 using acetic acid. 300 ppm of copper sulphate and 0.026M of the chelant to be tested are added to said composition. 10 ml of this solution is then mixed with 1 ml of hydrogen peroxide (35% active). The initial level of hydrogen peroxide is measured at this moment (t=0); the final level of hydrogen peroxide is measured after 30 minutes. The value of the ratio of the hydrogen peroxide concentration at t=0 and at t=30 nm is the Hydrogen Peroxide Decomposition Ratio (% Loss).

The initial and final level of hydrogen peroxide can be measured according to any standard technique. The following is a well-known and standard technique that was used by the inventors: 0.2–0.3 g (the exact quantity being precisely measured) of the solution to be titrated is added to 40 ml of 10% acetic acid. The autotitrator (Mettler DL58 Autotitrator) adds 20 ml of potassium iodide solution (15% in water), 5 ml of ammonium molybdate solution (2% in water) and titrates (while stirring) with 0.1M sodium thiosulphate solution. The level of hydrogen peroxide (% Peroxide) is then calculated from the following equation:

$$\% \text{ Peroxide} = \frac{\text{end-point (in ml)} \times \text{molarity of sodium thiosulphate} \times 34.02}{2 \times 10 \times \text{sample weight (in g)}}$$

34.02 being the molecular weight of Hydrogen Peroxide.

Three replicate runs are made at both t=0 and t=30 nm and then averaged to calculate the Hydrogen Peroxide Decomposition Ratio (% Loss).

Chelants having a Hydrogen Peroxide Decomposition Ratio (% Loss) of less than 10% are preferred for use herein. Preferably the value of the Hydrogen Peroxide Decomposition Ratio is less than 3.5%, more preferably less than 3%, even more preferably less than 2.0%.

Oxidative Hair Treatment Protocol

For each chelant tested, seven switches of virgin dark hair were used. "Virgin hair" means hair that has never been treated chemically and can be bought, for example, at Hugo Royer International Ltd, 10 Lakeside Business Park, Swan Park, Sandhurst, Berkshire, GU47 9ND. The switches usually weighed about 1.5 g each and are treated stepwise according to the following protocol.

A bleaching composition comprising the chelant to be tested is prepared by mixing in equal weight amounts a hydrogen peroxide emulsion base and an alkaline (high pH) emulsion base.

The hydrogen peroxide emulsion base contains:
 a) 35% by weight of an emulsion base premix comprising 10% stearyl alcohol and 5% cetereth25;
 b) 25% of an stabilizing solution comprising 1% tetrasodium DTPA, 0.4% HEDP, 1% sodium hydroxide (32% purity) and water q.s.p
 c) 14% of water;
 d) 26% of a solution of hydrogen peroxide (35% purity).

The alkaline emulsion base contains:
 a) 0.2% by weight of sodium sulphite;
 b) 0.2% of ascorbic acid;
 c) 3% of ammonium acetate;
 d) 44.5% of the same emulsion base premix used for the hydrogen peroxide emulsion base;
 e) 11% of an ammonia solution (30% purity) to set the pH to approximately 10;
 f) the amount to be tested of chelant or mixtures of chelants (for example 3.8% by weight of the alkaline emulsion base of EDDS, equivalent to 1.9% EDDS "on head");
 g) q.s. of water.

The pH of the mixture is buffered to 10 by the alkaline emulsion base.

2 g Of the bleaching composition per g of hair to be treated was applied on the hair switches and massaged in thoroughly. The hair switches were then wrapped in a plastic film and put in an oven at 30° C. After 30 nm, they were removed from the oven and from the wrapping film and rinsed for 1 mn in water. 0.1 g of shampoo per g. of hair was then added and milked for 30 s at a rate of at least 150 strokes a minute before rinsing for 30 s. The combined concentration of calcium and magnesium ions (water hardness) of the water used during all experiments (except for the preparation of the compositions tested, wherein water was distilled or dionised) was carefully kept at 9 grains per gallon (153 ppm), with a molar ratio of $Ca^{2+}/Mg^{2+}$ equal to 3:1. The concentration of copper ($Cu^{2+}$) ions was kept at about 1 ppm (+/−10%), the exact concentrations being measured by a standard analytic method. The rinsing water flow was adjusted to 6 liters per minute). The same shampooing and rinsing process was repeated another time (this is the "Oxidative Hair Treatment Protocol With 2 Intermediate Washes" referred to in the claims) or 9 additional times (this is the "Oxidative Hair Treatment Protocol With 10 Intermediate Washes" referred to in the claims) depending on the Damage Assessment Protocol used. The excess water was then squeezed out of the hair, and the hair dried with a fan. Any standard shampoo can be used in this protocol as long as it is free from transition metal ions such as copper ion and that the level chelants is less than 0.1% by weight of the shampoo. Prell® shampoo was using during these tests.

This Oxidative Hair Treatment Protocol can be repeated several times. When damage is measured according to the FT-IR Damage Assessing Protocol or to the Goniophotometer Damage Assessing Protocol (both described below) the Oxidative Hair Treatment Protocol is preferably repeated 5 times. This process is described as a 5-Cycle Oxidative Hair Treatment Protocol With 2 or 10 Intermediate Washes.

Damage Assessing Protocols

Two different test methods were used to assess the protection conferred to hair by the compositions according to the present invention. These methods (FT-IR and Goniophotometer Damage Assessing Protocol) are described in details below.

FT-IR Damage Assessing Protocol

Damage caused to the hair was assessed by the FT-IR (Fourier Transform Infrared) method, which has been established to be suitable for studying the effects of oxidative treatments on hair (Strassburger, J., *J. Soc. Cosmet. Chem.*, 36, 61–74 (1985); Joy, M. & Lewis, D. M., *Int. J. Cosmet. Sci.*, 13, 249–261 (1991); Signori, V. & Lewis, D. M., *Int. J. Cosmet. Sci.*, 19, 1–13 (1997)). In particular, these authors have shown that the method is suitable for quantifying the amount of cysteic acid that is produced from the oxidation of cystine. In general, the oxidation of cystine is thought to be a suitable marker by which to monitor the overall oxidation of the keratinous part of the fiber.

Net, the measurement of cysteic acid units by FT-IR is commonly used to study the effects of oxidative treatments or environmental oxidation upon keratin protein containing fibers such as hair and wool.

Signori & Lewis (D. M., *Int. J. Cosmet. Sci.*, 19, 1–13 (1997)) have shown that FT-IR using a diamond Attenuated Total Internal Reflection (ATR) cell is a sensitive and reproducible way of measuring the cysteic acid content of single fibers and bundles. They have shown that this technique is more suitable than using the FT-IR method in simple transmission or microscope modes. They have also shown that the diamond cell ATR was significantly more sensitive and reproducible than the ZnSE cell. Hence, the method that we have employed to measure the cysteic acid content of multiple fiber bundles and full hair switches, is based upon the FTIR diamond cell ATR method employed by Signori and Lewis (1997). The detailed description of the method used for testing the different damage inhibitors follows thereafter:

A Perkin Elmer Spectrum® 1 Fourier Transform Infrared (FTIR) system equipped with a diamond Attenuated Total Internal Reflection (ATR) cell was used to measure the cysteic acid concentration in human hair. In this method, hair switches of various sizes and colours can be used. The switches were platted (~1 plait per cm) in order to minimize variations in surface area of contact between readings. The Oxidative Hair Treatment Protocol described above was repeated for 5 cycles to mimic the behavior of hair after repeated bleaching cycles. Following this treatment, four readings per switch were taken (~⅓ and ⅔ s down the switch on both sides), and an average calculated. Backgrounds were collected every 4 readings, and an ATR cell pressure of 1N/m was employed. The cell was cleaned with ethanol between each reading, and a contamination check performed using the monitor ratio mode of the instrument. As prescribed by Signori & Lewis in 1997, a normalized double derivative analysis routine was used. The original spectra were initially converted to absorbance, before being normalized to the 1450 $cm^{-1}$ band (the characteristic and invariant protein $CH_2$ stretch). This normalized absorbance was then twice derivatised using a 13 point averaging. The value of the 1450 $cm^{-1}$ normalized $2^{nd}$ derivative of the absorbance at 1040 $cm^{-1}$ was taken as the relative concentration of cysteic acid. This figure was multiplied by $-1\times10^{-4}$ to recast it into suitable units. It was found that virgin human hair produced a value of ~20 cysteic acid units, and heavily oxidized hair produced values of >170. The following instrumental conditions were employed:

| | |
|---|---|
| Spectral Resolution | 4 $cm^{-1}$ |
| Data Interval | 0.7 $cm^{-1}$ |
| Mirror Scan Speed | 0.2 $cms^{-1}$ |
| Number of Background Scans | 20 |
| Number of Sample Scans | 20 |
| Scan Range | 4000 $cm^{-1}$ to 600 $cm^{-1}$ |

Using these instrumental conditions and the 2nd derivative analysis routine, it was found that the sensitivity and reproducibility of the method in the range 10 to 150 cysteic acid units, are both ~±5–10%.

Goniophotometer Damage Assessing Protocol

Damage caused to the hair was also assessed by the Goniophotometer method, which has been established to be suitable for studying the effects of changes in surface condition of the hair (R. F. Stamm, M. L. Garcia and J. J. Fuchs, 'The Optical Properties of Human Hair-I. Fundamental Consideration and Goniophotometer Curves', and 'II. The Lustre of Human Hair Fibres', J Soc. Cosmet. Chem. 28, 571–599 and 601–609 (September 1977)). It has been demonstrated that the shine (gloss or lustre) is proportional to the relative amounts of specularly and diffusely reflected light ($I_s$ and $I_d$ respectively). This is dictated by the refractive index of the fibre and the roughness of the surface. By coating the hair fibres in a very fine coating of gold before measuring the reflected light the internal reflection of the fibre is eliminated and the shine can be used as a sensitive measure of the roughness of the surface. For example, a smooth surface will reflect light that has a large specular content and a small diffuse content A GP200 Goniophotometer was used from Murakami Colour Research Laboratory. The gold coating was applied using an Emitech K-500 sputter coater.

Randomly chosen single fibres were loaded onto a single fibre holder (10 fibres per holder) and held in a parallel array. A minimum of 12 holders were loaded giving good reproducibility of +/-4%. Each single fibre holder was coated in gold using the Emitech sputter coater for 1 minute with a 25 mA coating rate. This gives a coating of between 10–300 nm of gold on the surface. The sample holder was then loaded into the GP200 Goniophotometer. The following instrumental conditions were employed:

Reflection measurement mode—fixed incident angle, variable receiving angle
Incidence Angle=+30
Detector Angle range=−30 to +60
Light aperture values: Incident=4.0; Receiving=2.0
Inclination of specimen table=0 deg
Sensitivity=850
High voltage of photomultiplier=725

For each set of fibres a reflectance spectrum is obtained. From this spectrum the reflectance peak maximum (Imax) is normalised to 1 and all the other reflectances are scaled according to this maximum $$I(norm)=I/Imax$$

Where I(norm)=normalised intensity, I=reflectance intensity, Imax=reflectance peak maximum.

The shine is calculated from the difference between the specular reflection and diffuse reflection at 0° divided by the width of the specular peak at its half maximum (in angular units)

$$S(norm)=[(1-I(0))/\sigma]*100$$

Where S(norm)=normalised shine, I(0)=normalised reflectance at 0°, σ=angular full width at half maximum in °.

COMPARATIVE TESTS

Damages Measured According to the FTIR-IR Damage Assessing Protocol

The following illustrates the effect of EDDS and 4 other chelants: ethylenediaminetetraacetic acid (EDTA), 1-hydroxyethane-1,1-diphosphonic acid (HEDP), diethylenetriaminepentaacetate (DTPA) and diethylenetriamine-N,N,N',N'',N''-penta(methylene phosphonate) (DTPMP). The weight percentages for each chelant are indicated in the first line of the table below. The tri-sodium salt of EDDS, tetra-sodium salt of EDTA, di-sodium salt of HEDP, penta-sodium salt of DTPA and tetra-sodium salt of DTPMP were used.

In this experiment EDDS was tested at 1.9% by weight on head, but EDDS also provides excellent benefits at much lower concentrations. Damage and lightening effects were assessed after 5 cycles according to the Oxidative Hair Treatment Protocol With 2 Intermediates Washes as described above. Human hair is often bleached or dyed 5 times or more during its life, which makes this 5 cycle test very meaningful. The results are shown in the table below:

| Weight % ("on-head") | 1.9% EDDS | 2.0% EDTA | 2.0% HEDP | 2.65% DTPA | 3.8% DTPMP |
|---|---|---|---|---|---|
| Damage after 5 cycles (cysteic acid units) | 110 | 165 | 163 | 147 | 142 |
| Damage benefit vs EDTA 2% | +33% | — | +1% | +11% | +14% |

Hair treated with 1.9% by weight EDDS displayed much less damage than hair treated with any other chelant. However increasing the level of any chelants allows reducing oxidative damage to value below 160 cysteic acid units. The value for damage without any added chelant is about 170 damaged cysteic units. The lightening effect of the oxidative composition was of about the same quality for all compositions.

Damages Measured by the Goniophotometer Damage Assessing Protocol

The following illustrates the effect of EDDS, HPPDS and 4 others chelants: EDTA, HEDP, DTPA and DTPMP. The tri-sodium salt of EDDS, tetra-sodium salt of HPPDS, tetra-sodium salt of EDTA, di-sodium salt of HEDP, penta-sodium salt of DTPA and tetra-sodium salt of DTPMP were used. The corresponding weight percentage is indicated in the first line of the table below. Damage was assessed after 5 cycles according to the Oxidative Hair Treatment Protocol With 10 Intermediate Washes described above (at least 11 measures for each chelant were made and averaged to give the values compiled below).

The normalized shine can slightly vary depending on the type of virgin hair used as starting material. In order to obtain data that are independent of the starting material, the normalized shine values obtained as described above have been subsequently divided by the value obtained for virgin (untreated) hair.

| Weight % | 0.95% EDDS | 0.97% HPPDS | 1.0% EDTA | 1.0% HEDP | 1.32% DTPA | 1.90% DTPMP |
|---|---|---|---|---|---|---|
| Normalized shine ratio (hair treated after 9 cycles/virgin hair) | 1.03 | 1.00 | 0.704 | 0.730 | 0.757 | 0.92 |

EXAMPLES

The following examples illustrate oxidative dye compositions according to the present invention and methods of manufacture thereof. It is understood that the examples and embodiments described herein are for illustrative purposes only and that various modifications or changes in light thereof will be suggested to one skilled in the art without departing from the scope of the present invention.

Examples of Formulation: Emulsion

| | 1 | 2 | 3 | 4 | 5 | 6 | 7 | 8 | 9 | 10 |
|---|---|---|---|---|---|---|---|---|---|---|
| Sodium sulphite | 0.1 | 0.1 | 0.1 | 0.1 | 0.1 | 0.1 | 0.1 | 0.1 | 0.1 | 0.1 |
| Ascorbic Acid | 0.1 | 0.1 | 0.1 | 0.1 | 0.1 | 0.1 | 0.1 | 0.1 | 0.1 | 0.1 |
| Ammonium Acetate | 1.5 | 1.5 | 1.5 | 1.5 | 1.5 | 1.5 | 1.5 | 1.5 | 1.5 | 1.5 |
| Ammonia (30% active) | 6.0 | 6.0 | 6.0 | 6.0 | 6.0 | 6.0 | 6.0 | 6.0 | 6.0 | 6.0 |
| Ceteareth 25 | 1.0 | 1.0 | 1.0 | 1.0 | 1.0 | 1.0 | 1.0 | 1.0 | 1.0 | 1.0 |
| Cetyl Alcohol | 1.6 | 1.6 | 1.6 | 1.6 | 1.6 | 1.6 | 1.6 | 1.6 | 1.6 | 1.6 |
| Stearyl Alcohol | 3.3 | 3.3 | 3.3 | 3.3 | 3.3 | 3.3 | 3.3 | 3.3 | 3.3 | 3.3 |
| Sodium Benzoate | 0.1 | 0.1 | 0.1 | 0.1 | 0.1 | 0.1 | 0.1 | 0.1 | 0.1 | 0.1 |
| Phenoxyethanol | 0.1 | 0.1 | 0.1 | 0.1 | 0.1 | 0.1 | 0.1 | 0.1 | 0.1 | 0.1 |
| DTPMP (tetrasodium salt of) | 2.5 | — | 2.5 | — | — | 1.0 | — | 1.0 | 0.5 | 3.0 |
| DTPA (pentasodium salt of) | — | — | 0.5 | 1.0 | — | — | 0.5 | — | 0.5 | — |
| EDDS (trisodium salt of) | — | 1.0 | — | 1.0 | 0.5 | 1.0 | 1.0 | 1.0 | 0.5 | — |
| Para-phenylene diamin | 0.8 | 0.5 | 0.6 | 0.5 | 0.8 | 0.8 | 0.5 | 0.6 | 0.5 | 0.8 |
| Para-aminophenol | 0.2 | 0.3 | 0.2 | 0.1 | 0.2 | 0.2 | 0.3 | 0.2 | 0.1 | 0.2 |
| Meta-aminophenol | 1.0 | 0.5 | 1.0 | 0.6 | 1.0 | 1.0 | 0.5 | 1.0 | 0.6 | 1.0 |
| Resorcinol | 1.6 | 1.2 | 1.6 | 0.8 | 1.6 | 1.6 | 1.2 | 1.6 | 0.8 | 1.6 |

-continued

|  | 1 | 2 | 3 | 4 | 5 | 6 | 7 | 8 | 9 | 10 |
|---|---|---|---|---|---|---|---|---|---|---|
| Hydrogen Peroxide (35% active) | 8.6 | 8.6 | 8.6 | 12.9 | 17 | 17 | 17 | 34 | 34 | 34 |
| Trimethylsilylamo-dimethicone (SF1708) | 0.5 | 0.5 | 1.5 | 2.0 | 2.0 | 2.0 | 2.0 | 2.0 | 2.0 | 2.0 |
| Polyquaternium 10 (Polymer JR30M) | 0.2 | 0.2 | — | 0.2 | 0.2 | 0.2 | 0.2 |  | — | — |
| Xanthan gum | 0.5 | 0.5 | — | 1.0 | 0.5 | 0.5 | 0.5 | 0.5 | 0.5 | 1.0 |
| Cetyl hydroxyethyl Cellulose (Natrosol 330CS Plus) | — | — | 0.8 | 1.0 | 0.8 | 0.5 | 0.5 | 0.5 | 0.5 | 1.0 |
| pH adjust to pH 10 | qs | qs | qs | qs | qs | qs | qs | qs | qs | qs |
| Water | qs | qs | qs | qs | qs | qs | qs | qs | qs | qs |

Examples of Formulation: Thickened Aqueous Solution

|  | 1 | 2 | 3 | 4 | 5 | 6 | 7 | 8 | 9 | 10 |
|---|---|---|---|---|---|---|---|---|---|---|
| Sodium sulphite | 0.1 | 0.1 | 0.1 | 0.1 | 0.1 | 0.1 | 0.1 | 0.1 | 0.1 | 0.1 |
| Ascorbic Acid | 0.1 | 0.1 | 0.1 | 0.1 | 0.1 | 0.1 | 0.1 | 0.1 | 0.1 | 0.1 |
| Citric Acid | 1.0 | 1.0 | 1.0 | 1.0 | 1.0 | 1.0 | 1.0 | 1.0 | 1.0 | 1.0 |
| Ammonia (30% active) | 6.0 | 6.0 | 6.0 | 6.0 | 6.0 | 6.0 | 6.0 | 6.0 | 6.0 | 6.0 |
| Acrylates Copolymer (Aculyn ® 33A) | 2.4 | 2.4 | 2.4 | 2.4 | 2.4 | 2.4 | 2.4 | 2.4 | 2.4 | 2.4 |
| Oleth 10 | 1.0 | 1.0 | 1.0 | 1.0 | 1.0 | 1.0 | 1.0 | 1.0 | 1.0 | 1.0 |
| Oleth 2 | 0.8 | 0.8 | 0.8 | 0.8 | 0.8 | 0.8 | 0.8 | 0.8 | 0.8 | 0.8 |
| Oleic Acid | 0.9 | 0.9 | 0.9 | 0.9 | 0.9 | 0.9 | 0.9 | 0.9 | 0.9 | 0.9 |
| Cocamide DEA | 3.0 | 3.0 | 3.0 | 3.0 | 3.0 | 3.0 | 3.0 | 3.0 | 3.0 | 3.0 |
| DTPMP (tetrasodium salt of) | 2.5 | — | 2.5 | — | — | 1.0 | — | 1.0 | 0.5 | 3.0 |
| DEPTA (pentasodium salt of) | — | — | 0.5 | 1.0 | — | — | 0.5 | — | 0.5 | — |
| EDDS (trisodium salt of) | — | 1.0 | — | 1.0 | 0.5 | 1.0 | 1.0 | 1.0 | 0.5 | — |
| Para-phenylene diamine | 0.8 | 0.5 | 0.6 | 0.5 | 0.8 | 0.8 | 0.5 | 0.6 | 0.5 | 0.8 |
| Para-aminophenol | 0.2 | 0.3 | 0.2 | 0.1 | 0.2 | 0.2 | 0.3 | 0.2 | 0.1 | 0.2 |
| Meta-aminophenol | 1.0 | 0.5 | 1.0 | 0.6 | 1.0 | 1.0 | 0.5 | 1.0 | 0.6 | 1.0 |
| Resorcinol | 1.6 | 1.2 | 1.6 | 0.8 | 1.6 | 1.6 | 1.2 | 1.6 | 0.8 | 1.6 |
| Hydrogen Peroxide (35% active) | 8.6 | 8.6 | 8.6 | 13 | 17 | 17 | 17 | 34 | 34 | 34 |
| Behentrimonium Chloride | 0.5 | 0.5 | 1.5 | 2.0 | 2.0 | 2.0 | 2.0 | 2.0 | 2.0 | 2.0 |
| Dicetyldimonium Chloride | 0.2 | 0.2 | 0.7 | 0.2 | 0.2 | 0.2 | 0.2 | — | — | — |
| Acrylates Steareth-20 Methacrylate Copolymer (Aculyn ® 22) | 0.5 | 0.5 | — | 1.0 | 0.5 | 0.5 | 0.5 | 0.5 | 0.5 | 1.0 |
| Propylene Glycol | 8.2 | 8.2 | 8.2 | 8.2 | 8.2 | 8.2 | 8.2 | 8.2 | 8.2 | 8.2 |
| Ethoxy Diglycol | 4.2 | 4.2 | 4.2 | 4.2 | 4.2 | 4.2 | 4.2 | 4.2 | 4.2 | 4.2 |
| pH adjust to pH 10 | qs | qs | qs | qs | qs | qs | qs | qs | qs | qs |
| Water | qs | qs | qs | qs | qs | qs | qs | qs | qs | qs |

The above compositions are useful for dyeing hair with reduced damage. Similar compositions not including oxidative dye precursors and couplers (in the above examples para-aminophenol, meta-aminophenol and resorcinol) can be used for bleaching (lightening) hair.

Oxidative hair dye compositions are usually sold in kits comprising, in separate containers, a dye component (also called "dye cream" for emulsion or "dye liquid" for solution) comprising the oxidative dye precursors (and usually the Hair Swelling Agent) and a hydrogen peroxide component (also called "hydrogen peroxide cream" for emulsion or "hydrogen peroxide liquid" for solution) comprising the oxidizing agent (usually hydrogen peroxide). The consumer mixes the dye component and hydrogen peroxide component immediately before use. The examples of the tables above illustrate the resulting mixtures.

Similarly, bleaching compositions are usually sold as a kit comprising two or three separate containers. The first contains the hair-swelling agent (e.g. ammonia), the second contains the oxidizing agent and the third (optional) contains a second oxidizing agent (e.g. alkali or ammonium salt of persulphates, percarbonate, perborate). The bleaching compositions are obtained by mixing the above-mentioned compositions immediately before use.

These kits are well known in the art and the composition in each container can be manufactured utilizing any one of the standard approaches, these include:

Oil in water process

Phase Inversion process

One-pot process

The chelants are usually added to a proportion of the water at the start of the making process at ambient temperature, and allowed to dissolve. The fatty components are then added and the mixture is processed as is normal for the above outlined procedures. For example, in a 1 pot process the polymers and chelants would be predissolved in water, the fatty materials added and then the whole heated to about 70–80° C.

A controlled cooling and optional shearing process to form the final structured product in the case of an emulsion would then follow. Addition of the ammonia and pH trimming complete the making process of the dye cream.

In the case of a liquid solution comprising acrylate polymers, these would be formulated into the hydrogen peroxide component. The glycol solvents and fatty components are formulated into the dye component. A structured product is formed when the dye and hydrogen peroxide components are mixed together prior to use of the composition, through deprotonation of the polymer acrylic acid groups yielding a polymeric micro-gel. Further details on the manufacture of these two-part aqueous composition for coloring hair, which forms a gel on mixing of the two parts can be found in U.S. Pat. No. 5,376,146, Casperson et al. and U.S. Pat. No. 5,393,305, Cohen et al.

The composition of the present invention can also be formulated as 2-part aqueous compositions comprising polyetherpolyurethane as thickening agent (such as Aculyn® (46) as described in U.S. Pat. No. 6,156,076, Casperson et al. and U.S. Pat. No. 6,106,578, Jones.

When the compositions of different containers are mixed before use and the resulting mixture comprises the chelants claimed, there is no preference on how the chelants are distributed in these containers. Obviously chelants that can be altered by hydrogen peroxide (or any oxidizing agent used) such as secondary amine chelants should however be formulated in the dye component. The hydrogen peroxide component should however preferably comprise at least about 0.1% of a stable chelant to stabilize hydrogen peroxide. This stabilizer is required to prevent the hydrogen peroxide from decomposing too rapidly. For example EDTA can be used in the hydrogen peroxide component as stabilizer.

METHODS OF USE

It is understood that the examples of methods of use and embodiments described herein are for illustrative purposes only and that various modifications or changes in light thereof will be suggested to one skilled in the art without departing from the scope of the present invention.

Without Pretreatment

The chelants according to the present invention are preferably formulated directly in the oxidizing compositions applied on hair (e.g. oxidative dye compositions or bleaches).

Oxidative Dye

Oxidative dye compositions are usually sold as a kit comprising at least two separate containers: one contains the oxidative dye precursors with the hair-swelling agent (e.g. ammonia) in a suitable carrier (e.g. dye cream or liquid) and the other contains the oxidizing agent in a suitable carrier (e.g. hydrogen peroxide cream or liquid). The consumer prepares the oxidative dye composition immediately before use by mixing both compositions and applies it on hair. After working the mixture a few minutes (to insure uniform application to all of the hair), the oxidative dye composition is allowed to remain on the hair for an amount sufficient for the dyeing to take place (usually about 30 minutes). The consumer then rinses his/her hair thoroughly with tap water and allows it to dry. It is observed that the hair has changed from its original color to the desired color.

When present, the optional conditioning agent can be packaged partly or in totality in a third container. In this case, all three compositions can be mixed immediately before use and applied together, or the content of the third container can be applied (after an optional rinse step) as a post-treatment immediately after the oxidative dye composition resulting from the mixture of the other containers.

Bleaching Compositions

Bleaching compositions are usually sold as a kit comprising two or three separate containers. The first contains the hair-swelling agent (e.g. ammonia), the second contains the oxidizing agent and the third (optional) contains a second oxidizing agent (e.g. alkali or ammonium salt of persulphates, percarbonate, perborate). The consumer prepares the bleaching compositions immediately before use by mixing all compositions and applies the mixture on hair (as for the oxidative dye composition) for an amount of time sufficient for the bleaching to take place (usually about 30 nm).

In this kind of kit comprising at least two containers there is no preference on the distribution of the chelants and conditioners in the containers, although it is preferred that the composition comprising the oxidizing agent comprises at least a small amount of chelant (which is not necessary a phosphonate chelant) to stabilize the oxidizing agent.

As for oxidative dye compositions, the optional conditioning agent can be packaged partly or in totality in a third container. In this case, all three compositions can be mixed immediately before use and applied together, or the content of the third container can be applied (after an optional rinse step) as a post-treatment immediately after the oxidative dye composition resulting from the mixture of the other containers.

With Pretreatment

The chelants can also be applied to hair as a pre-treatment. The pretreatment composition ("first composition") can be applied immediately before the oxidizing composition ("second composition") or after a longer period of time.

Pretreatment Immediately Followed by an Oxidizing Composition

In the case of a pretreatment applied on hair and immediately followed by the oxidizing composition, said pretreatment composition can be rinsed off hair before the application of the oxidizing composition, but will be preferably kept on the hair during the application of the oxidizing compositions, the resulting mixture being rinsed off following the oxidizing step. Kits comprising one container for the first composition (pre-treat) and one, two or more containers for the second composition (oxidizing composition) can be advantageously used for this method. Two containers or more can be required for the second composition in case this second composition is prepared immediately before use by mixing the content of two containers or more (e.g. oxidative hair dye composition or bleaching composition). The kit can also comprise an additional container for a composition comprising a conditioning agent that is applied independently from the second composition in a third step, optionally following a rinsing step.

Color Care

The pretreatment can also take place as a "color care" treatment anytime between two oxidative treatments but not immediately prior to one. The 2 oxidative treatments are preferably separated by at least one day, more preferably at least one week. Oxidative hair dye treatments are generally repeated about once a month and obviously, hair will be usually rinsed with water immediately after each oxidative treatment. The "color care" treatment can be repeated as many times as practical between the two oxidative treatments, which can be once, twice or more.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is, therefore, intended to cover in the appended claims all such changes and modifications that are within the scope of this invention.

What is claimed is:

1. A composition suitable for treating hair comprising:
   a) an oxidizing agent; and
   b) a chelant (L) having a $$\frac{\log K_{CuL}}{\log K_{CaL}}$$

ratio calculated at pH 10 of at least about 3.20, wherein log $K_{CuL}$ is the common logarithm of the Conditional Stability Constant of said chelant with $Cu^{2+}$ and log $K_{CaL}$ is the common logarithm of the Conditional Stability Constant of said chelant with $Ca^{2+}$;
   wherein said chelant is an aminocarboxylic acid chelant selected from the group consisting of ethylenediamine-N,N'-disuccinic acid (EDDS), ethylenediamine-N,N'diglutaric acid (EDDG), 2-hydroxypropylenediamine-N,N'-disuccinic acid (HPDDS), glycinamide-N,N'-disuccinic acid (GADS), ethylenediamine-N-N'-bis(ortho-hydroxyphenyl acetic acid) (EDDHA), and salts thereof, derivatives thereof and mixtures thereof; and
   wherein said chelant is in an amount sufficient to provide a Normalized Shine Ratio of at least about 0.95 as measured by the Goniophotometer Damage Assessing Protocol after a 5-Cycle Hair Oxidative Treatment Protocol With 10 Intermediate Washes.

2. A composition according to claim 1, wherein said chelant (L) has a Hydrogen Peroxide Decomposition Ratio (% Loss) of less than about 10% as measured by the Hydrogen Peroxide Decomposition Ratio Measurement Protocol.

3. A composition according to claim 1, wherein said chelant (L) is capable of fonning a hexadendate complex with $Cu^{2+}$.

4. A composition according to claim 1, wherein said oxidizing agent is present at a level of from about 0.1% to about 40% by weight of the composition and is selected from water-soluble oxidizing agents and mixtures thereof.

5. A composition according to claim 1, further comprising at least one oxidative hair dye precursor.

6. A composition according to claim 1, wherein said composition is in the form of an oil-in-water emulsion.

7. A composition according to claim 1, wherein said composition is in the form of a thickened aqueous solution.

8. A composition according to claim 1, wherein said composition has a pH from about 8 to about 12.

9. A method of treating hair, said method comprising the steps of:
   i) applying a first composition comprising an oxidizing agent;
   ii) applying a second composition comprising a chelant (L) having a $$\frac{\log K_{CuL}}{\log K_{CaL}}$$

ratio calculated at pH 10 of at least about 3.20, wherein log $K_{CuL}$ is the common logarithm of the Conditional Stability Constant of said chelant with $Cu^{2+}$ and log $K_{CaL}$ is the common logarithm of the Conditional Stability Constant of said chelant with $Ca^{2+}$:
   wherein said chelant is an aminocarboxylic acid chelant selected from the group consisting of ethylenediamine-N,N'-disuccinic acid (EDDS), ethylenediamine-N,N'-diglutaric acid (EDDG) 2-hydroxypropylenediamine-N,N'-disuccinic acid (HPDDS), glycinamide-N,N'-disuccinic acid (GADS), ethylenediamine-N-N'-bis(ortho-hydroxyphenyl acetic acid) (EDDHA), and salts thereof, derivatives thereof and mixtures thereof; and
   wherein said chelant is in an amount sufficient to provide a Normalized Shine Ratio of at least about 0.95 as measured by the Goniophotometer Damage Assessing Protocol after a 5-Cycle Hair Oxidative Treatment Protocol With 10 Intermediate Washes; and
   iii) applying a third composition comprising a second oxidizing agent; and
   wherein steps i) and iii) are separated by at least 1 day and step ii) does not take place immediately before step iii).

10. A method of treating hair, said method comprising the steps of:
    i) applying to the hair a first composition comprising a chelant (L) having a $$\frac{\log K_{CuL}}{\log K_{CaL}}$$

ratio calculated at pH 10 of at least about 3.20, wherein log $K_{CuL}$ is the common logarithm of the Conditional Stability Constant of said chelant with $Cu^{2+}$ and log $K_{CaL}$ is the common logarithm of the Conditional Stability Constant of said chelant with $Ca^{2+}$;
    wherein said chelant is an aminocarboxylic acid chelant selected from the group consisting of ethylenediamine-N,N'-disuccinic acid EDDS), ethylenediamine-N,N'-diglutaric acid (EDDG), 2-hydroxypropylenediamine-N,N'-disuccinic acid (HPDDS), glycinamide -N,N'-disuccinic acid (GADS), ethylenediamine-N-N'-bis(ortho-hydroxyphenyl acetic acid) (EDDHA), and salts thereof, derivatives thereof and mixtures thereof; and
    wherein said chelant is in an amount sufficient to provide a Normalized Shine Ratio of at least about 0.95 as measured by the Goniophotometer Damage Assessing Protocol after a 5-Cycle Hair Oxidative Treatment Protocol With 10 Intermediate Washes; and ii) applying to the hair a second composition comprising an oxidizing agent;

wherein step i) takes place before step ii).

11. A method of treating hair according to claim 10, wherein step i) takes place immediately before step ii).

12. A method of treating hair according to claim 10, wherein said first composition is not rinsed off the hair before said second composition is applied to the hair.

13. A kit for treating hair comprising:
i) a first separately packaged composition comprising a chelant (L) having a $$\frac{\log K_{CuL}}{\log K_{CaL}}$$

ratio calculated at pH 10 of at least about 3.20, wherein log $K_{CuL}$ is the common logarithm of the Conditional Stability Constant of said chelant with $Cu^{2+}$ and log $K_{CaL}$ is the common logarithm of the Conditional Stability Constant of said chelant with $Ca^{2+}$;

wherein said chelant is an aminocarboxylic acid chelant selected from the group consisting of ethylenediamine-N,N'-disuccinic acid (EDDS), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N-N'-bis(ortho-hydroxyphenyl acetic acid) (EDDHA), and salts thereof, derivatives thereof and mixtures thereof; and wherein said chelant is in an amount sufficient to provide a Normalized Shine Ratio of at least about 0.95 as measured by the Goniophotometer Damage Assessing Protocol after a 5-Cycle Hair Oxidative Treatment Protocol With 10 Intermediate Washes; and ii) a second separately packaged composition comprising an oxidizing agent.

14. A kit for dyeing hair comprising a first and a second compositions packaged in different containers, wherein said first composition comprises an oxidizing agent and said second composition comprises an oxidative dye precursor, wherein the resulting mixture of said first and second compositions is a composition according to claim 5.

15. A method of dyeing human hair, said method comprising the steps of:
i) mixing the first and second composition of a kit according to claim 14;
ii) applying the mixture obtained after step i) to hair;
iii) massaging said mixture into hair;
iv) retaining said mixture on the hair for an amount of time sufficient for mixture to dye the hair;
iv) rinsing off said composition with water.

* * * * *